(12) United States Patent
Yamada et al.

(10) Patent No.: US 9,693,559 B2
(45) Date of Patent: Jul. 4, 2017

(54) HERBICIDAL COMPOSITION

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 15/054,628

(22) Filed: Feb. 26, 2016

(65) Prior Publication Data

US 2016/0174561 A1 Jun. 23, 2016

Related U.S. Application Data

(63) Continuation of application No. 14/398,289, filed as application No. PCT/JP2013/062649 on Apr. 30, 2013, now Pat. No. 9,380,783.

(30) Foreign Application Priority Data

May 8, 2012 (JP) .................................. 2012-107101

(51) Int. Cl.
  *A01N 25/00* (2006.01)
  *A01N 43/54* (2006.01)
  *A01N 43/66* (2006.01)
  *A01N 47/36* (2006.01)
  *A01N 37/34* (2006.01)
  *A01N 37/40* (2006.01)
  *A01N 41/10* (2006.01)
  *A01N 43/40* (2006.01)

(52) U.S. Cl.
  CPC ............. *A01N 47/36* (2013.01); *A01N 37/34* (2013.01); *A01N 37/40* (2013.01); *A01N 41/10* (2013.01); *A01N 43/40* (2013.01)

(58) Field of Classification Search
  None
  See application file for complete search history.

(56) References Cited

U.S. PATENT DOCUMENTS

| | | | |
|---|---|---|---|
| 5,612,284 A | 3/1997 | Boyles et al. | |
| 5,849,665 A | 12/1998 | Gut et al. | |
| 6,046,134 A | 4/2000 | De Gennaro et al. | |
| 7,968,498 B2 | 6/2011 | Threewitt et al. | |
| 9,380,783 B2 * | 7/2016 | Yamada | A01N 47/36 |
| 2003/0176284 A1 | 9/2003 | Hacker et al. | |
| 2003/0186816 A1 | 10/2003 | Hacker et al. | |
| 2004/0023803 A1 | 2/2004 | Jager et al. | |
| 2004/0033897 A1 * | 2/2004 | Haas | A01N 61/00 504/255 |
| 2011/0166023 A1 | 7/2011 | Nettleton-Hammond et al. | |

FOREIGN PATENT DOCUMENTS

| | | |
|---|---|---|
| DE | 19919951 | 4/1999 |
| EP | 237292 | 9/1987 |
| EP | 0303383 | 2/1989 |
| EP | 1 842 426 | 10/2007 |
| EP | 2832223 | 2/2015 |
| JP | 2-76803 | 3/1990 |
| JP | 2004-507476 | 3/2004 |
| JP | 2004-99602 | 4/2004 |
| JP | 2005-526736 | 9/2005 |
| JP | 2005-527507 | 9/2005 |
| WO | 90/15535 | 12/1990 |
| WO | 93/21772 | 11/1993 |
| WO | 94/27438 | 12/1994 |
| WO | 97/48276 | 12/1997 |
| WO | 2005/055714 | 6/2005 |
| WO | 2008/142391 | 11/2008 |
| WO | 2010/001084 | 1/2010 |

OTHER PUBLICATIONS

Partial Supplementary European Search Report for European Application No. 13788253.6, dated Feb. 1, 2016.
Ya et al., Tank Mixtures of Herbicides for Maize Protection, Zashchita Karantin Rasteni, No. 1, pp. 20-22, 2009.
International Search Report mailed Jul. 2, 2013 in PCT/JP2013/06249.
Third Party Observation submitted Dec. 2, 2013 in PCT/JP2013/06249.
Peak® 75WG Herbicide, label, Syngenta, pp. 1-13 and p. 1, Apr. 2006.
Gilles Quesnel, Improved 2002 Guide to Weed, Crop Talk, vol. 2, No. 2, pp. 1-11, Feb. 2002.
Top Crop Manager, Weed Control Guide 2011, Syngenta Canada, pp. 1-24, Mar. 2011.
Extended European Search Report in respect to European Application No. 13788253.6, dated Apr. 28, 2016.
Hennigh et al., Postemergence weed control in acetolactate synthase-resistant grain sorghum, Weed Technology (2010), 24(3), 219-225, Abs.
Krausz et al., Total postemergence weed control in imidazolinone-resistant corn (Zea mays), Weed Technology (1998), 12(1), 151-156, Abs.

* cited by examiner

*Primary Examiner* — Alton Pryor
(74) *Attorney, Agent, or Firm* — Greenblum & Bernstein, P.L.C.

(57) ABSTRACT

To provide a high active herbicidal composition having a broad herbicidal spectrum.
A herbicidal composition comprising (a) nicosulfuron or its salt, (b) prosulfuron or its salt and (c) at least one herbicidal compound selected from the group consisting of mesotrione, bicyclopyrone, dicamba, dicamba ester, bromoxynil, bromoxynil ester and their salts.

12 Claims, No Drawings

HERBICIDAL COMPOSITION

CROSS-REFERENCE TO RELATED APPLICATIONS

The present application is a continuation of U.S. application Ser. No. 14/398,289, which is a national stage of international patent application no. PCT/JP2013/062649, filed Apr. 30, 2013, which claims priority of JP 2012-107101, filed May 8, 2012. The entire disclosures of these applications are expressly incorporated by reference herein.

TECHNICAL FIELD

The present invention relates to a herbicidal composition comprising (a) nicosulfuron or its salt (hereinafter referred to as compound A), (b) prosulfuron or its salt (hereinafter referred to as compound B) and (c) at least one herbicidal compound selected from the group consisting of mesotrione, bicyclopyrone, dicamba, dicamba ester, bromoxynil, bromoxynil ester and their salts (hereinafter referred to as compound C).

BACKGROUND ART

Patent Document 1 discloses a herbicidal composition comprising compound B and a specific known herbicide. Further, Patent Document 2 discloses a herbicidal composition comprising 2-[4-(methylsulfonyl)-2-nitrobenzoyl]-1,3-cyclohexanedione and a specific known herbicide.

Further, Patent Document 3 discloses a herbicidal composition comprising bicyclopyrone and a specific known herbicide.

However, any of the above Patent Documents does not disclose a herbicidal composition comprising a specific combination of compound A, compound B and compound C as herbicidally active ingredients of the present invention, and does not specifically disclose a remarkable synergistic effect obtained by the combination.

PRIOR ART DOCUMENTS

Patent Documents

Patent Document 1: WO93/21772
Patent Document 2: WO97/48276
Patent Document 3: EP1842426

DISCLOSURE OF INVENTION

Technical Problem

At present, many herbicidal compositions have been developed and used, but there are a variety of types of undesired plants represented by weeds to be controlled. Further, undesired plants having lowered sensitivity to herbicides (herbicide-resistant weeds) emerged, and in some applications, practically, herbicides have only insufficient effects.

The object of the present invention is to provide a high active herbicidal composition having a broader herbicidal spectrum, and a method for controlling undesired plants or inhibiting their growth using it.

Solution to Problem

The present inventors have conducted extensive studies to solve the above problems and as a result, found that unexpectedly excellent herbicidal effects can be obtained by combination of specific compound A, compound B and compound C which are herbicidally active ingredients of the present invention, as compared with a case where the respective compounds are applied individually or two compounds are used in combination (for example, compound A and compound C are used in combination), and accomplished the present invention.

That is, the present invention relates to a herbicidal composition comprising compound A, compound B and compound C as herbicidally active ingredients.

The present invention further relates to a method for controlling undesired plants or inhibiting their growth, which comprises applying a herbicidally effective amount of the herbicidal composition to the undesired plants or to a place where they grow.

The present invention further relates to a method for controlling undesired plants or inhibiting their growth, which comprises applying a herbicidally effective amount of compound A, a herbicidally effective amount of compound B and a herbicidally effective amount of compound C, to the undesired plants or to a place where they grow.

Advantageous Effects of Invention

The herbicidal composition of the present invention is capable of controlling a wide range of undesired plants emerging in agricultural fields or non-agricultural fields. It has a remarkable herbicidal activity when a composition comprising compound A and compound B, and compound C as a specific third herbicidally active ingredient are used in combination. It represents a synergistic effect i.e. a herbicidal effect higher than the mere addition of the herbicidal effect of the combination of compound A and compound B and the herbicidal effect of the third herbicidally active ingredient.

That is, the herbicidal composition of the present invention can be applied at a low dose as compared with a case where the respective active ingredients are applied individually. Thus, it is effective to reduce the environmental load on an area where the composition is applied or a surrounding area thereof.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E^1=(\alpha+\beta)-(\alpha\beta)/100$$

Similarly, the activity expected by the combination of three active ingredients can be calculated as follows.

$$E^2=(\alpha+\beta+\gamma)-(\alpha\beta+\alpha\gamma+\beta\gamma)/100+(\alpha\beta\gamma)/10,000$$

where α: growth inhibition rate when treated with x (g/ha) of herbicide X,

β: growth inhibition rate when treated with y (g/ha) of herbicide Y,

γ: growth inhibition rate when treated with z (g/ha) of herbicide Z, $E^1$: growth inhibition rate expected when treated with x (g/ha) of herbicide X and y (g/ha) of herbicide Y.

$E^2$: growth inhibition rate expected when treated with x (g/ha) of herbicide X, y (g/ha) of herbicide Y, and z (g/ha) of herbicide Z.

That is, when the actual growth inhibition rate (measured value) is larger than the growth inhibition rate by the above calculation (calculated value), the activity by the combination can be regarded as showing a synergistic effect.

The herbicidal composition of the present invention shows a synergistic effect when calculated by the above formula.

DESCRIPTION OF EMBODIMENTS

As for compound A, nicosulfuron (common name) is 2-(4,6-dimethoxypyrimidin-2-ylcarbamoylsulfamoyl)-N,N-dimethylnicotinamide.

As for compound B, prosulfuron (common name) is 1-(4-methoxy-6-methyl-1,3,5-triazin-2-yl)-3-[2-(3,3,3-trifluoropropyl)phenylsulfonyl]urea.

As for compound C, mesotrione (common name) is 2-(4-mesyl-2-nitrobenzoyl)cyclohexane-1,3-dione.

As for compound C, bicyclopyrone (common name) is 4-hydroxy-3-{2-[(2-methoxyethoxy)methyl]-6-(trifluoromethyl)-3-pyridylcarbonyl}bicyclo[3.2.1]oct-3-en-2-one.

As for compound C, dicamba (common name) is a compound disclosed in The Pesticide Manual Sixteenth Edition, pages 319 to 321. Its ester or a salt thereof may, for example, be dicamba-methyl, dicamba-butotyl, dicamba-diglycolamine, dicamba-dimethylammonium, dicamba-diolamine, dicamba-isopropylammonium, dicamba-potassium or dicamba-sodium.

As for compound C, bromoxynil (common name) is a compound disclosed in The Pesticide Manual Sixteenth Edition, pages 131 to 134. Its ester or a salt thereof may, for example, be bromoxynil-heptanoate, bromoxynil-octanoate or bromoxynil-potassium.

The salt included in compound A, compound B and compound C may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of the respective compounds in the present invention cannot generally be defined, as it varies depending upon various conditions such as the type of the formulation, the weather conditions, and the type and the growth stage of the undesired plants. The mixing ratio of compound A to compound B is, for example, from 75:1 to 1:15, preferably from 40:1 to 1:5 by the weight ratio. Further, the mixing ratio of compound A to compound C is, for example, from 15:1 to 1:100, preferably from 4:1 to 1:50 by the weight ratio.

In a case where compound C is mesotrione or its salt, the mixing ratio of compound A to compound C is preferably from 4:1 to 1:15 by the weight ratio.

By using the combination of compound A and compound B and further mesotrione in combination in a mixing ratio of compound A to mesotrione of from 4:1 to 1:15, particularly excellent effects (for example, a synergistic effect) will be obtained as compared with another mixing ratio.

In a case where compound C is bicyclopyrone or its salt, the mixing ratio of compound A to compound C is preferably from 4:1 to 1:40 by the weight ratio.

By using the combination of compound A and compound B and further bicyclopyrone in combination in a mixing ratio of compound A to bicyclopyrone of from 4:1 to 1:40, particularly excellent effects (for example, a synergistic effect) will be obtained as compared with another mixing ratio.

In a case where compound C is dicamba, its ester or a salt thereof, the mixing ratio of compound A to compound C is preferably from 2:1 to 1:40 by the weight ratio.

By using the combination of compound A and compound B and further dicamba, its ester or a salt thereof in combination in a mixing ratio of compound A to dicamba, its ester or a salt thereof of from 2:1 to 1:40, particularly excellent effects (such as a synergistic effect) will be obtained as compared with another mixing ratio.

In a case where compound C is bromoxynil, its ester or a salt thereof, the mixing ratio of compound A to compound C is preferably from 1:1 to 1:50 by the weight ratio.

By using the combination of compound A and compound B and further bromoxynil, its ester or a salt thereof in combination in a mixing ratio of compound A to bromoxynil, its ester or a salt thereof of from 1:1 to 1:50, particularly excellent effects (such as a synergistic effect) will be obtained as compared with another mixing ratio.

The herbicidally effective amounts of compounds A, B and C cannot generally be defined, as they vary depending upon various conditions such as the mixing ratios of the respective compounds, the type of the formulation, the weather conditions, and the type and the growth stage of the undesired plants.

For example, compound A is applied in an amount of from 5 to 150 g/ha, preferably from 10 to 100 g/ha, compound B is applied in an amount of from 2 to 75 g/ha, preferably from 2.5 to 50 g/ha, and compound C is applied in an amount of from 10 to 500 g/ha, preferably from 25 to 500 g/ha.

In a case where compound C is mesotrione or its salt, the herbicidally effective amount of compound C is preferably from 25 to 150 g/ha.

In a case where compound C is bicyclopyrone or its salt, the herbicidally effective amount of compound C is preferably from 25 to 400 g/ha.

In a case where compound C is dicamba, its ester or a salt thereof, the herbicidally effective amount of compound C is preferably from 50 to 400 g/ha.

In a case where compound C is bromoxynil, its ester or a salt thereof, the herbicidally effective amount of compound C is preferably from 100 to 500 g/ha.

The herbicidal composition of the present invention may be applied to undesired plants or may be applied to a place where they grow. Further, it may be applied at any time either before or after the emergence of the undesired plants.

Further, the herbicidal composition of the present invention may take various application forms such as soil application, foliar application, irrigation application, and submerged application.

Further, it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically cyperaceae such as sedge (*Cyperus* spp.) (such as purple nutsedge (*Cyperus rotundus* L.), smallflower umbrella sedge (*Cyperus difformis* L.), yellow nutsedge (*Cyperus esculentus* L.) or amur cyperus (*Cyperus microiria* Steud.)) or spikesedge (*Kyllinga* spp.) (such as green kyllinga (*Kyllinga brevifolia* Rottb. var.

leiolepis)); gramineae such as barnyard grass (*Echinochloa* spp.) (such as barnyardgrass (*Echinochloa crus-galli* L.), early watergrass (*Echinochloa oryzicola* vasing.) or Japanese millet (*Echinochloa utilis* Ohwi et Yabuno)), crabgrass (*Digitaria* spp.) (such as summergrass (*Digitaria ciliaris* (Retz.) Koel), large crabgrass (*Digitaria sanguinalis* L.), violet crabgrass (*Digitaria violascens* Link) or Jamaican crabgrass (*Digitaria horizontalis* Willd.)), goosegrass (*Eleusine* spp.) (such as goosegrass (*Eleusine indica* L.)), ryegrass (*Lolium* spp.) (such as italian ryegrass (*Lolium multiflorum* Lam.)), foxtail (*Setaria* spp.) (such as green foxtail (*Setaria viridis* (L.))), sorghum (*Sorghum* spp.) (such as johnsongrass (*Sorghum halepense* (L.) Pers.) or shattercane (*Sorghum bicolor* (L.) Moench.)), oat (*Avena* spp.) (such as wild oat (*Avena fatua* L.)), brome (*Bromus* spp.) (such as drooping brome (*Bromus tectorum* L.) or japanese brome (*Bromus japonicus* Thunb.)), meadowgrass (*Poa* spp.) (such as annual bluegrass (*Poa annus* L.)), foxtail grass (*Alopecurus* spp.) (such as blackgrass (*Alopecurus myosuroides* Huds.), shortawn foxtail (*Alopecurus aequalis* Sobol. var. *amurensis*)), bermudagrass (*Cynodon dactylon* (L.) Pers.), panic grass (*Panicum* spp.) (such as guinea grass (*Panicum maximum* Jacq.) or fall panicum (*Panicum dichotomiflorum* (L.) Michx.)), signal grass (*Brachiaria* spp.) (such as plantain signal grass (*Brachiaria plantaginea* (LINK) Hitchc.), palisade signal grass (*Brachiaria decumbens* Stapf) or mauritius signal grass (*Brachiaria mutica* (Forssk.) Stapf)), paspalum (*Paspalum* spp.) (such as dallisgrass (*Paspalum dilatatum* Poir.) or vasey's grass (*Paspalum urvillei* Steud.)), itchgrass (*Rottboellia* spp.) (such as itchgrass (*Rottboellia cochinchinensis* (LOUR.) W. D. CLAYTON)), or sandbur (*Cenchrus* spp.) (such as southern sandbur (*Cenchrus echinatus* L.)); scrophulariaceae such as persian speedwell (*Veronica persica* Poir.) or corn speedwell (*Veronica arvensis* L.); compositae such as beggar ticks (*Bidens* spp.) (such as hairy beggarticks (*Bidens pilosa* L.), devils berggarticks (*Bidens frondosa* L.) or *Bidens biternata* (Lour.) Merr. et Sherff, beggarticks (*Bidens subalternans* DC.)), hairy fleabane (*Conyza bonariensis* (L.) Cronq.), dandelion (*Taraxacum officinale* Weber), horseweed (*Conyza* spp.) (such as canadian horseweed (*Conyza canadensis* (L.) Cronquist)), cocklebur (*Xanthium* spp.) (such as common cocklebur (*Xanthium strumarium* L.)), ragweed (*Ambrosia* spp.) (such as annual ragweed (*Ambrosia artemisiifolia* L.)), ragwort (*Senecio* spp.) (such as old-man-in-the-spring (*Senecio vulgaris* L.)); leguminosae such as rattlepod or rattlebox (*Crotalaria* spp.) (such as sunn-hemp (*Crotalaria juncea* L.)), poison bean (*Sesbania* spp.) (such as rostrate sesbania (*Sesbania rostrata* Bremek. & Oberm.) or sesbania pea (*Sesbania cannabina* (Retz.) Pers.)), common lespedeza (*Lespedeza striata* (Thunb.) Hook. et Arn.), korean lespedeza (*Kummerowia stipulacea* (Maxim.) Makino) or white clover (*Trifolium repens* L.)); caryophyllaceae such as sticky chickweed (*Cerastium glomeratum* Thuill.) or starwort (*Stellaria* spp.) (such as common chickweed (*Stellaria media* L.)); euphorbiaceae such as garden spurge (*Euphorbia hirta* L.), threeseeded copperleaf (*Acalypha australis* L.) or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly sida (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea quamoclit* L.), *Ipomoea grandifolia* (DAMMERMANN) O'DONNELL, hairy merremia (*Merremia aegyptia* (L.) URBAN) or field bindweed (*Convolvulus arvensis* L.); chenopodiaceae such as goosefoot (*Chenopodium* spp.) (such as common lambsquarters (*Chenopodium album* L.)); portulacaceae such as common purslane (*Portulaca oleracea* L.); amaranthaceae such as pigweed (*Amaranthus* spp.) (such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol.), powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.)), ataco (*Amaranthus quitensis* Kunth.) or roughfruit amaranth (*Amaranthus rudis* Sauer.)); solanaceae such as nightshade (*Solanum* spp.) (such as black nightshade (*Solanum nigrum* L.)); polygonaceae such as knotweed (*Polygonum* spp.) (such as spotted knotweed (*Polygonum lapathifolium* L.) or green smartweed (*Polygonum scabrum* MOENCH)); cruciferae such as flexuous bittercress (*Cardamine flexuosa* WITH.), or mustard (*Sinapis* spp.) (such as Charlock (*Sinapis arvensis* L.)); cucurbitaceae such as burcucumber (*Sicyos angulatus* L.); commelinaceae such as common dayflower (*Commelina communis* L.); rosaceae such as mock strawberry (*Duchesnea chrysantha* (Zoll. et Mor.) Miq.); molluginacea such as carpetweed (*Mollugo verticillata* L.); or rubiaceae such as false cleavers (*Galium spurium* var. echinospermon (Waft.) Hayek) or stickywilly (*Galium aparine* L.).

The herbicidal composition of the present invention is very useful in practical application, and for example, the following cases may be mentioned.

(1) It has a remarkable synergistic effect, and has a favorable herbicidal activity even if the doses of the respective compounds A, B and C are small, and accordingly the impact on the surrounding environment can be suppressed.

(2) A herbicidal composition having a long lasting herbicidal effect i.e. a long lasting residual activity, as compared with a case where compound A, compound B and compound C are applied individually, or two compounds are used in combination (for example, compound A and compound C are used in combination) may be provided.

(3) A herbicidal composition having a broad spectrum having high effects against both gramineae and broad leaf weeds, as compared with a case where compound A, compound B and compound C are applied individually, or two compounds are used in combination (for example, compound A and compound C are used in combination), may be provided.

(4) Annual and perennial gramineae such as *Echinochloa* spp., *Digitaria* spp., *Setaria* spp., *Poa* spp., *Avena* spp., *Agropyron* spp., *Alopecurus* spp., *Eleusine* spp., *Rottboellia* spp., *Sorghum* spp. and *Panicum* spp., which are problematic as noxious weeds in agricultural fields, particularly corn fields, can be controlled.

(5) It has a high herbicidal activity also against weeds in late leaf stage, such as weeds in 8-leaf stage, and particularly remarkable for gramineae.

(6) It has a favorable herbicidal activity against gramineae and broad leaf weeds either by foliar application or soil application.

(7) It has a high herbicidal activity against weeds having lowered sensitivity to ALS (acetolactate synthase) inhibitors, such as cyperaceae, amaranthaceae, compositae, cruciferae, caryophyllaceae, and gramineae.

(8) It has a high herbicidal activity against weeds having lowered sensitivity to PSII (photosystem II) inhibitors, such as gramineae, chenopodiaceae, amaranthaceae, solanaceae, malvaceae, compositae, and polygonaceae.

(9) It has a high herbicidal activity against weeds having lowered sensitivity to 4-HPPD inhibitors, such as amaranthaceae.

In consideration of the application site of the herbicidal composition or the type or growth state of the undesired plants, the herbicidal composition of the present invention may be mixed with or may be used in combination with other herbicides, fungicides, antibiotics, plant hormones, insecticides, fertilizers, phytotoxicity-reducing agents, etc., in addition to the above active ingredients, without departing from the intention and the scope of the present invention, whereby more excellent effects and activities may sometimes be obtained.

Such other herbicides may, for example, be (1) those which are believed to exhibit herbicidal effects by disturbing hormone activities of plants, (2) those which are believed to exhibit herbicidal effects by inhibiting photosynthesis of plants, (3) those which are believed to be converted to free radicals by themselves to form active oxygen in the plant body and show rapid herbicidal efficacy, (4) those which are believed to exhibit herbicidal effects by inhibiting chlorophyll biosynthesis of plants and abnormally accumulating a photosensitizing peroxide substance in the plant body, (5) those which are believed to exhibit herbicidal effects characterized by bleaching activities by inhibiting chromogenesis of plants such as carotenoids, (6) those which exhibit strong herbicidal effects specifically to gramineous plants, (7) those which are believed to exhibit herbicidal effects by inhibiting an amino acid biosynthesis of plants, (8) those which are believed to exhibit herbicidal effects by inhibiting cell mitoses of plants, (9) those which are believed to exhibit herbicidal effects by inhibiting protein biosynthesis or lipid biosynthesis of plants, and (10) those which are believed to exhibit herbicidal effects by being parasitic on plants.

The herbicidal composition of the present invention may be prepared by mixing compound A, compound B and compound C, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A, compound B and compound C may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins; and a transesterified vegetable oil such as methylated rapeseed oil or ethylated rapeseed oil. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredients to such various additives in the herbicidal composition of the present invention may be from 0.001:99.999 to 95:5, preferably from about 0.005:99.995 to about 90:10.

As a method of applying the herbicidal composition of the present invention, a proper method can be employed among various methods depending upon various conditions such as the application site, the type of the formulation, and the type and the growth stage of the undesired plants to be controlled.

For example, the following methods may be mentioned.

(1) Compound A, compound B and compound C are separately formulated, and the formulations are applied to plants to be controlled as they are or as diluted to predetermined concentrations with e.g. water as the case requires, and as the case requires, as mixed with a spreader (such as a surfactant, a vegetable oil or a mineral oil).

(2-1) Compound A and compound B are formulated together, and compound C is formulated, and the formulations are applied to plants to be controlled as they are or as diluted to predetermined concentrations with e.g. water, and as the case requires, as mixed with a spreader (such as a surfactant, a vegetable oil or a mineral oil).

(2-2) Compound A and compound C are formulated together, and compound B is formulated, and the formulations are applied to plants to be controlled as they are or as diluted to predetermined concentrations with e.g. water, and as the case requires, as mixed with a spreader (such as a surfactant, a vegetable oil or a mineral oil).

(2-3) Compound B and compound C are formulated together, and compound A is formulated, and the formulations are applied to plants to be controlled as they are or as diluted to predetermined concentrations with e.g. water, and as the case requires, as mixed with a spreader (such as a surfactant, a vegetable oil or a mineral oil).

(3) Compound A, compound B and compound C are formulated together, and the formulation is applied to plants to be controlled as it is or as diluted to a predetermined concentration with e.g. water, and as the case requires, as mixed with a spreader (such as a surfactant, a vegetable oil or a mineral oil).

In the above application methods (1) and (2-1) to (2-3), the respective formulations may be mixed when diluted to predetermined concentrations with e.g. water so that they are applied to plants to be controlled simultaneously, or they may be applied continuously or with an appropriate interval. In order to obtain effects of the present invention more effectively, it is preferred to apply compound A, compound B and compound C simultaneously.

Preferred embodiments of the present invention will be described below, but the present invention is by no means restricted thereto.

(1) A herbicidal composition comprising (a) nicosulfuron or its salt, (b) prosulfuron or its salt and (c) at least one herbicidal compound selected from the group consisting of mesotrione, bicyclopyrone, dicamba, dicamba ester, bromoxynil, bromoxynil ester and their salts.

(2) The herbicidal composition according to the above (1), which contains (a), (b) and (c) in amounts to show a herbicidally synergistic effect (synergistic herbicidally effective amount).

(3) The herbicidal composition according to the above (1), wherein the weight ratio of (a) to (b) is within a range of from 75:1 to 1:15, and the weight ratio of (a) to (c) is within a range of from 15:1 to 1:100.

(4) The herbicidal composition according to the above (1), wherein the weight ratio of (a) to (b) is within a range of from 40:1 to 1:5, and the weight ratio of (a) to (c) is within a range of from 4:1 to 1:50.

(5) The herbicidal composition according to the above (1), which contains, as herbicidal compounds (herbicidally active ingredients), only (a), (b) and (c).

(6) The herbicidal composition according to the above (5), which contains only (a), (b) and (c) and an additive for formulation which does not have a herbicidal effect by itself.

(7) The herbicidal composition according to the above (5), wherein the additive for formulation is at least one member selected from the group consisting of a surfactant, a carrier, a solvent, a vegetable oil, a mineral oil and a transesterified vegetable oil.

(8) A method for controlling undesired plants or inhibiting their growth, which comprises a herbicidally effective amount of a herbicidal composition comprising (a), (b) and (c), to the undesired plants or to a place where they grow.

(9) A method for controlling undesired plants or inhibiting their growth, which comprises applying a herbicidally effective amount of (a), a herbicidally effective amount of (b) and a herbicidally effective amount of (c) to the undesired plants or to a place where they grow.

(10) The method according to the above (8) or (9), wherein the undesired plants are weeds having lowered sensitivity to herbicidal compounds.

(11) The method according to the above (8) or (9), wherein the undesired plants are weeds having lowered sensitivity to ALS (acetolactate synthase) inhibitors.

(12) The method according to the above (8) or (9), which comprises applying (a) in an amount to show a herbicidally synergistic effect (synergistic herbicidally effective amount), (b) in an amount to show a herbicidally synergistic effect (synergistic herbicidally effective amount) and (c) in an amount to show a herbicidally synergistic effect (synergistic herbicidally effective amount).

(13) The method according to the above (8) or (9), wherein (a) is applied in an amount of from 5 to 150 g/ha, (b) is applied in an amount of from 2 to 75 g/ha, and (c) is applied in an amount of from 10 to 500 g/ha.

(14) The method according to the above (8) or (9), wherein (a) is applied in an amount of from 10 to 100 g/ha, (b) is applied in an amount of from 2.5 to 50 g/ha, and (c) is applied in an amount of from 25 to 500 g/ha.

(15) The method according to the above (8) or (9), wherein the application is for soil treatment.

(16) The method according to the above (8) or (9), wherein the undesired plants are strongly noxious weeds in corn fields.

(17) The method according to the above (8) or (9), wherein the undesired plants are weeds in a stage before emergence to 8-leaf stage.

(18) The method according to the above (8) or (9), wherein the undesired plants are annual or perennial gramineae.

(19) The herbicidal composition according to the above (1), wherein (c) is at least one herbicidal compound selected from the group consisting of bicyclopyrone, dicamba, dicamba ester, bromoxynil, bromoxynil ester and their salts.

(20) The herbicidal composition according to the above (1), wherein (c) is at least one herbicidal compound selected from the group consisting of mesotrione, bicyclopyrone and their salts.

(21) The herbicidal composition according to the above (1), wherein (c) is at least one herbicidal compound selected from the group consisting of bromoxynil, bromoxynil ester and their salts.

(22) The herbicidal composition according to the above (1), wherein (c) is mesotrione or its salt.

(23) A herbicide against convolvulaceae, solanaceae, gramineae, leguminosae, compositae or malvaceae, which comprises (a), (b) and (c) as defined in the above (1).

(24) A herbicide against convolvulaceae or solanaceae, which comprises (a), (b) and (c) as defined in the above (1).

(25) The herbicidal composition according to the above (1), which is used to control convolvulaceae, solanaceae, gramineae, leguminosae, compositae or malvaceae, or to inhibit their growth.

(26) The herbicidal composition according to the above (1), which is used to control convolvulaceae or solanaceae, or to inhibit their growth.

(27) A method for controlling undesired plants or inhibiting their growth, which comprises applying a herbicidally effective amount of (a) nicosulfuron or its salt, a herbicidally effective amount of (b) prosulfuron or its salt and a herbicidally effective amount of (c) at least one herbicidal compound selected from the group consisting of mesotrione, bicyclopyrone, dicamba, dicamba ester, bromoxynil, bromoxynil ester and their salts, to the undesired plants or to a place where they grow.

(28) The method according to the above (27), wherein the undesired plants are convolvulaceae, solanaceae, gramineae, leguminosae, compositae or malvaceae.

(29) The method according to the above (27), wherein the undesired plants are convolvulaceae or solanaceae.

(30) The method according to the above (27), wherein the undesired plants are annual or perennial gramineae.

EXAMPLES

Now, the present invention will be described in detail with reference to the following Examples. However, it should be understood that the present invention is by no means restricted thereto.

In Test Examples, as nicosulfuron, a flowable containing nicosulfuron as an active ingredient (tradename: ONEHOPE NYUZAI, manufactured by Ishihara Sangyo Kaisha, Ltd.) was used.

As prosulfuron, water dispersible granules containing prosulfuron as an active ingredient (tradename: Peak, manufactured by Syngenta) were used.

As mesotrione, a flowable containing mesotrione as an active ingredient (tradename: Callisto, manufactured by Syngenta) was used.

As dicamba, water dispersible granules containing dicamba as an active ingredient (tradename: Celebrity B, manufactured by BASF) were used.

As bicyclopyrone, a wettable powder containing bicyclopyrone prepared by a conventional method was used.

As bromoxynil-octanoate, an emulsifiable concentrate containing bromoxynil-octanoate as an active ingredient (tradename: Certrol B, manufactured by Bayer CropScience) was used.

Test Example 1

Upland field soil was put into a 1/300,000 ha pot, and seeds of sunn-hemp (*Crotalaria juncea* L.) were sown. On the next day, predetermined amounts of the above formulations respectively containing nicosulfuron, prosulfuron and mesotrione were diluted with water (in an amount corresponding to 1,000 L/ha) and applied for soil treatment by a small sprayer.

On the 28th day after treatment, the state of growth of the sunn-hemp was visually observed to determine the growth inhibition rate (%) in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate of sunn-hemp (%) | |
|---|---|---|---|
| | | Measured value | Calculated value |
| Nicosulfuron | 10 | 30 | — |
| Prosulfuron | 50 | 60 | — |
| Mesotrione | 150 | 30 | — |
| Nicosulfuron + Prosulfuron + Mesotrione | 10 + 50 + 150 | 100 | 80 |

Test Example 2

Upland field soil was put into a 1/300,000 ha pot, and seeds of wild oat (*Avena fatua* L.) were sown. On the next day, predetermined amounts of the above formulations respectively containing nicosulfuron, prosulfuron and mesotrione were diluted with water (in an amount corresponding to 1,000 L/ha) and applied for soil treatment by a small sprayer.

On the 28th day after treatment, the state of growth of the wild oat was visually observed to determine the growth inhibition rate (%). The growth inhibition rate (%) (measured value) and the growth inhibition rate (%) calculated in the same manner as in the above Test Example 1 are shown in Table 2.

TABLE 2

| Compound | Dose (g/ha) | Growth inhibition rate of wild oat (%) | |
|---|---|---|---|
| | | Measured value | Calculated value |
| Nicosulfuron | 100 | 80 | — |
| Prosulfuron | 2.5 | 0 | — |
| Mesotrione | 25 | 0 | — |
| | 150 | 0 | — |
| Nicosulfuron + Prosulfuron + Mesotrione | 100 + 2.5 + 25 | 90 | 80 |
| | 100 + 2.5 + 150 | 85 | 80 |

Test Example 3

Upland field soil was put into a 1/300,000 ha pot, and seeds of wild oat (*Avena fatua* L.) were sown. On the next day, predetermined amounts of the above formulations respectively containing nicosulfuron, prosulfuron and mesotrione were diluted with water (in an amount corresponding to 1,000 L/ha) and applied for soil treatment by a small sprayer.

On the 28th day after treatment, the state of growth of the wild oat was visually observed to determine the growth inhibition rate (%). The growth inhibition rate (%) (measured value) and the growth inhibition rate (%) calculated in the same manner as in the above Test Example 1 are shown in Table 3.

TABLE 3

| Compound | Dose (g/ha) | Growth inhibition rate of wild oat (%) | |
|---|---|---|---|
| | | Measured value | Calculated value |
| Nicosulfuron | 30 | 70 | — |
| Prosulfuron | 15 | 0 | — |
| Mesotrione | 50 | 0 | — |
| Nicosulfuron + Prosulfuron + Mesotrione | 30 + 15 + 50 | 80 | 70 |

Test Example 4

Upland field soil was put into a 1/300,000 ha pot, and seeds of prickly sida (*Sida spinosa* L.) were sown. On the next day, predetermined amounts of the above formulations respectively containing nicosulfuron, prosulfuron, dicamba and bicyclopyrone were diluted with water (in an amount corresponding to 1,000 L/ha) and applied for soil treatment by a small sprayer.

On the 28th day after treatment, the state of growth of the prickly sida was visually observed to determine the growth inhibition rate (%). The growth inhibition rate (%) (measured value) and the growth inhibition rate (%) calculated in the same manner as in the above Test Example 1 are shown in Table 4.

TABLE 4

| Compound | Dose (g/ha) | Growth inhibition rate of prickly sida (%) | |
|---|---|---|---|
| | | Measured value | Calculated value |
| Nicosulfuron | 10 | 10 | — |
| | 30 | 10 | — |
| | 100 | 20 | — |
| Prosulfuron | 2.5 | 20 | — |
| | 15 | 20 | — |
| | 50 | 40 | — |
| Dicamba | 50 | 0 | — |
| | 150 | 20 | — |
| | 400 | 40 | — |
| Bicyclopyrone | 25 | 25 | — |
| Nicosulfuron + | 10 + 50 + 50 | 100 | 46 |
| Prosulfuron + | 10 + 50 + 400 | 100 | 68 |
| Dicamba | 100 + 2.5 + 50 | 50 | 36 |
| | 100 + 2.5 + 400 | 100 | 62 |
| | 30 + 15 + 150 | 100 | 42 |
| Nicosulfuron + | 10 + 50 + 25 | 99 | 60 |
| Prosulfuron + Bicyclopyrone | 100 + 2.5 + 25 | 70 | 52 |

Test Example 5

Upland field soil was put into a 1/300,000 ha pot, and seeds of black nightshade (*Solanum nigrum* L.) were sown. On the next day, predetermined amounts of the above formulations respectively containing nicosulfuron, prosulfuron and bromoxynil-octanoate were diluted with water (in an amount corresponding to 1,000 L/ha) and applied for soil treatment by a small sprayer.

On the 28th day after treatment, the state of growth of the black nightshade was visually observed to determine the growth inhibition rate (%). The growth inhibition rate (%) (measured value) and the growth inhibition rate (%) calculated in the same manner as in the above Test Example 1 are shown in Table 5.

TABLE 5

| Compound | Dose (g/ha) | Growth inhibition rate of black nightshade (%) | |
|---|---|---|---|
| | | Measured value | Calculated value |
| Nicosulfuron | 10 | 20 | — |
| Prosulfuron | 50 | 20 | — |
| Bromoxynil-octanoate | 100 | 0 | — |
| | 500 | 0 | — |
| Nicosulfuron + | 10 + 50 + 100 | 83 | 36 |
| Prosulfuron + Bromoxynil-octanoate | 10 + 50 + 500 | 93 | 36 |

Test Example 6

Upland field soil was put into a 1/300,000 ha pot, and seeds of annual ragweed (*Ambrosia artemisiifolia* L.) were sown. On the next day, predetermined amounts of the above formulations respectively containing nicosulfuron, prosulfuron and bromoxynil-octanoate were diluted with water (in an amount corresponding to 1,000 L/ha) and applied for soil treatment by a small sprayer.

On the 28th day after treatment, the state of growth of the annual ragweed was visually observed to determine the growth inhibition rate (%). The growth inhibition rate (%) (measured value) and the growth inhibition rate (%) calculated in the same manner as in the above Test Example 1 are shown in Table 6.

TABLE 6

| Compound | Dose (g/ha) | Growth inhibition rate of annual ragweed (%) | |
|---|---|---|---|
| | | Measured value | Calculated value |
| Nicosulfuron | 30 | 0 | — |
| | 100 | 0 | — |
| Prosulfuron | 2.5 | 78 | — |
| | 15 | 93 | — |
| Bromoxynil-octanoate | 100 | 0 | — |
| | 200 | 0 | — |
| | 500 | 0 | — |
| Nicosulfuron + | 100 + 2.5 + 100 | 99 | 78 |
| Prosulfuron + | 100 + 2.5 + 500 | 100 | 78 |
| Bromoxynil-octanoate | 30 + 15 + 200 | 100 | 93 |

Test Example 7

Upland field soil was put into a 1/300,000 ha pot, and seeds of ivy-leaved morningglory (*Ipomoea hederacea* (L.) Jacq.) were sown. On the next day, predetermined amounts of the above formulations respectively containing nicosulfuron, prosulfuron and bicyclopyrone were diluted with water (in an amount corresponding to 1,000 L/ha) and applied for soil treatment by a small sprayer.

On the 14th day after treatment, the state of growth of the ivy-leaved morningglory was visually observed to determine the growth inhibition rate (%). The growth inhibition rate (%) (measured value) and the growth inhibition rate (%) calculated in the same manner as in the above Test Example 1 are shown in Table 7.

TABLE 7

| Compound | Dose (g/ha) | Growth inhibition rate of ivy-leaved morningglory (%) | |
|---|---|---|---|
| | | Measured value | Calculated value |
| Nicosulfuron | 10 | 0 | — |
| Prosulfuron | 50 | 50 | — |
| Bicyclopyrone | 25 | 5 | — |
| | 400 | 25 | — |
| Nicosulfuron + | 10 + 50 + 25 | 88 | 53 |
| Prosulfuron + Bicyclopyrone | 10 + 50 + 400 | 100 | 63 |

Test Example 8

Upland field soil was put into a 1/300,000 ha pot, and seeds of korean lespedeza (*Kummerowia stipulacea* (Maxim.) Makino) were sown. On the next day, predetermined amounts of the above formulations respectively containing nicosulfuron, prosulfuron and bicyclopyrone were diluted with water (in an amount corresponding to 1,000 L/ha) and applied for soil treatment by a small sprayer.

On the 28th day after treatment, the state of growth of the korean lespedeza was visually observed to determine the growth inhibition rate (%). The growth inhibition rate (%)

(measured value) and the growth inhibition rate (%) calculated in the same manner as in the above Test Example 1 are shown in Table 8.

TABLE 8

| Compound | Dose (g/ha) | Growth inhibition rate of korean lespedeza (%) | |
|---|---|---|---|
| | | Measured Value | Calculated value |
| Nicosulfuron | 100 | 30 | — |
| Prosulfuron | 2.5 | 50 | — |
| Bicyclopyrone | 400 | 78 | — |
| Nicosulfuron + Prosulfuron + Bicyclopyrone | 100 + 2.5 + 400 | 98 | 92 |

Test Example 9

Upland field soil was put into a 1/1,000,000 ha pot, and seeds of annual ragweed (*Ambrosia artemisiifolia* L.) were sown. When the annual ragweed reached 6.0 to 8.0-leaf stage, predetermined amounts of the above formulations respectively containing nicosulfuron, prosulfuron and mesotrione were diluted with water (in an amount corresponding to 300 L/ha) and applied for foliar treatment by a small sprayer.

On the 14th day after treatment, the state of growth of the annual ragweed was visually observed to determine the growth inhibition rate (%). The growth inhibition rate (%) (measured value) and the growth inhibition rate (%) calculated in the same manner as in the above Test Example 1 are shown in Table 9.

TABLE 9

| Compound | Dose (g/ha) | Growth inhibition rate of annual ragweed (%) | |
|---|---|---|---|
| | | Measured value | Calculated value |
| Nicosulfuron | 30 | 0 | — |
| Prosulfuron | 10 | 55 | — |
| | 15 | 53 | — |
| Mesotrione | 75 | 25 | — |
| Nicosulfuron + Prosulfuron + Mesotrione | 30 + 10 + 75 | 73 | 66 |
| | 30 + 15 + 75 | 76 | 64 |

Test Example 10

Upland field soil was put into a 1/1,000,000 ha pot, and seeds of common *lespedeza* (*Lespedeza striata* (Thunb.) Hook. et Arn.) were sown. When the common *lespedeza* reached 4.0-leaf stage, predetermined amounts of the above formulations respectively containing nicosulfuron, prosulfuron and dicamba were diluted with water (in an amount corresponding to 300 L/ha) and applied for foliar treatment by a small sprayer.

On the 14th day after treatment, the state of growth of the common *lespedeza* was visually observed to determine the growth inhibition rate (%). The growth inhibition rate (%) (measured value) and the growth inhibition rate (%) calculated in the same manner as in the above Test Example 1 are shown in Table 10.

TABLE 10

| Compound | Dose (g/ha) | Growth inhibition rate of common lespedeza (%) | |
|---|---|---|---|
| | | Measured value | Calculated value |
| Nicosulfuron | 30 | 5 | — |
| Prosulfuron | 10 | 10 | — |
| | 15 | 13 | — |
| Dicamba | 100 | 23 | — |
| | 150 | 50 | — |
| Nicosulfuron + Prosulfuron + Dicamba | 30 + 10 + 100 | 63 | 34 |
| | 30 + 15 + 100 | 68 | 36 |
| | 30 + 10 + 150 | 68 | 57 |
| | 30 + 15 + 150 | 70 | 58 |

Test Example 11

Upland field soil was put into a 1/1,000,000 ha pot, and seeds of velvetleaf (*Abutilon theophrasti* Medic.) were sown. When the velvetleaf reached 5.0 to 5.3-leaf stage, predetermined amounts of the above formations respectively containing nicosulfuron, prosulfuron, dicamba, bromoxyniloctanoate and bicyclopyrone were diluted with water (in an amount corresponding to 300 L/ha) and applied for foliar treatment by a small sprayer.

On the 20th day after treatment, the state of growth of the velvetleaf was visually observed to determine the growth inhibition rate (%). The growth inhibition rate (%) (measured value) and the growth inhibition rate (%) calculated in the same manner as in the above Test Example 1 are shown in Table 11.

TABLE 11

| Compound | Dose (g/ha) | Growth inhibition rate of velvetleaf (%) | |
|---|---|---|---|
| | | Measured value | Calculated value |
| (Nicosulfuron + prosulfuron) | (30 + 15) | 55 | — |
| Dicamba | 150 | 8 | — |
| Bromoxynil-octanoate | 200 | 5 | — |
| Bicyclopyrone | 100 | 40 | — |
| (Nicosulfuron + prosulfuron) + Dicamba | (30 + 15) + 150 | 63 | 58 |
| (Nicosulfuron + prosulfuron) + Bromoxynil-octanoate | (30 + 15) + 200 | 73 | 57 |
| (Nicosulfuron + prosulfuron) + Bicyclopyrone | (30 + 15) + 100 | 83 | 73 |

By using nicosulfuron and prosulfuron and further a specific third component in combination, a high herbicidal activity and further a synergistic effect were obtained as compared with use of nicosulfuron and prosulfuron in combination.

INDUSTRIAL APPLICABILITY

According to the present invention, a herbicidal composition having a broad herbicidal spectrum, having high activity and having a long lasting effect, is provided, broadening of the herbicidal spectrum particularly against gramineae and application to genetically-modified crops resistant to ALS inhabitance, etc. are possible, and an increase in the application site can be expected.

Further, the present invention can meet requirements by practical users that development of resistance is to be delayed by use of active ingredients differing in the mechanism in combination, against weeds which have acquired resistance due to repeated application of a specific herbicide.

The entire disclosure of Japanese Patent Application No. 2012-107101 filed on May 8, 2012 including specification, claims and summary is incorporated herein by reference in its entirety.

What is claimed is:

1. A herbicidal composition comprising (a) nicosulfuron or its salt, (b) prosulfuron or its salt and (c) bicyclopyrone or its salt, wherein the mixing ratio of (a) to (b) is from 75:1 to 1:15 by the weight ratio, and the mixing ratio of (a) to (c) is from 15:1 to 1:100 by the weight ratio wherein a combination of said a, b and c exhibits synergy.

2. The herbicidal composition according to claim 1, wherein the mixing ratio of (a) to (b) is from 40:1 to 1:5 by the weight ratio, and the mixing ratio of (a) to (c) is from 4:1 to 1:40 by the weight ratio.

3. A method for controlling undesired plants or inhibiting their growth, which comprises applying a herbicidally effective amount of (a) nicosulfuron or its salt, a herbicidally effective amount of (b) prosulfuron or its salt, and a herbicidally effective amount of (c) bicyclopyrone or its salt, to the undesired plants or to a place where they grow, wherein the mixing ratio of (a) to (b) is from 75:1 to 1:15 by the weight ratio, and the mixing ratio of (a) to (c) is from 15:1 to 1:100 by the weight ratio wherein the applying of said a, b and c together exhibits synergy.

4. The method according to claim 3, wherein the mixing ratio of (a) to (b) is from 40:1 to 1:5 by the weight ratio, and the mixing ratio of (a) to (c) is from 4:1 to 1:40 by the weight ratio.

5. The method according to claim 3, wherein (a) is applied in an amount of from 5 to 150 g/ha, (b) is applied in an amount of from 2 to 75 g/ha, and (c) is applied in an amount of from 10 to 500 g/ha.

6. The method according to claim 4, wherein the (a) is applied in an amount of from 10 to 100 g/ha, (b) is applied in an amount of from 2.5 to 50 g/ha, and (c) is applied in an amount of from 25 to 400 g/ha.

7. The method according to claim 3, wherein the undesired plants are strongly noxious weeds in corn fields.

8. The method according to claim 3, wherein the undesired plants are weeds having lowered sensitivity to herbicidal compounds.

9. The method according to claim 3, wherein the undesired plants are weeds in a stage before emergence to 8-leaf stage.

10. The method according to claim 3, wherein the undesired plants are convolvulaceae, solanaceae, gramineae, leguminosae, compositae, or malvaceae.

11. The method according to claim 3, wherein the undesired plants are convolvulaceae or solanaceae.

12. The method according to claim 3, wherein the undesired plants are annual or perennial gramineae.

* * * * *